US00PP32417P3

(12) United States Plant Patent
Leis et al.

(10) Patent No.: US PP32,417 P3
(45) Date of Patent: Nov. 3, 2020

(54) APPLE TREE NAMED 'CIVPEAK'

(50) Latin Name: ***Malus domestica* Borkh**
Varietal Denomination: CIVPEAK

(71) Applicant: C.I.V.—CONSORZIO ITALIANO VIVAISTI-SOCIETÀ CONSORTILE A R.L., Comacchio FE (IT)

(72) Inventors: Michelangelo Leis, Ferrara (IT); Alessio Martinelli, Ferrara (IT)

(73) Assignee: C.I.V.—CONSORZIO ITALIANO VIVAISTI—SOCIETA CONSORTILE A R.L., Comacchio (IT)

( * ) Notice: Subject to any disclaimer, the term of this patent is extended or adjusted under 35 U.S.C. 154(b) by 0 days.

(21) Appl. No.: 16/350,229

(22) Filed: Oct. 18, 2018

(65) Prior Publication Data

US 2020/0128713 P1 Apr. 23, 2020

(51) Int. Cl.
*A01H 5/02* (2018.01)
*A01H 6/74* (2018.01)

(52) U.S. Cl.
USPC ..... Plt./161
CPC ..... *A01H 6/74* (2018.05)

(58) Field of Classification Search
USPC ..... Plt./161
CPC ..... A01H 5/0875
See application file for complete search history.

(56) References Cited

PUBLICATIONS

Printout of application information from UPOV Pluto Database for corresponding CPVO application No. 2016/3221 filed Dec. 19, 2016 (1 page) (http://www.upov.int/pluto/en/).
Printout of application information from UPOV Pluto Database for corresponding Switzerland application No. 17-3117 filed Feb. 8, 2017 (1 page) (http://www.upov.int/pluto/en/).
Printout of application information from UPOV Pluto Database for corresponding CPVO application No. 2017/0941 filed Mar. 31, 2017 (1 page) (http://www.upov.int/pluto/en/).
Printout of application information from UPOV Pluto Database for corresponding Serbia application No. 320-04-03993/2017-11 filed May 17, 2017 (1 page) (http://www.upov.int/pluto/en/).

*Primary Examiner* — Kent L Bell
(74) *Attorney, Agent, or Firm* — Foley & Lardner LLP

(57) ABSTRACT

A new and distinct *Malus domestica* Borkh apple tree variety named 'CIVPEAK', particularly characterized by a medium overall vigor, spreading habit, and easy management. The fruit has a conical shape, and regular size. The skin is flushed and mottled with a purple-red overcolor on 80-90% of a yellow background surface. The flesh is very firm, crunchy, and juicy. The taste is balanced with a good level of acidity.

4 Drawing Sheets

Latin name of the genus and species of the plant claimed: *Malus domestica* Borkh.
Variety denomination: 'CIVPEAK'.

BACKGROUND OF THE INVENTION

The present invention relates to a new and distinct variety of Apple tree, botanically known as *Malus domestica* Borkh of the Rosaceae family, and hereinafter referred to by the name 'CIVPEAK'.

The new *Malus* variety was discovered and selected by the inventors Alessio Martinelli and Michelangelo Leis, as a bud mutation of 'CIVNI' (Patented, U.S. Plant Pat. No. 14,177) located on reproductive brindle with fruiting apical bud growing in a cultivated area in 2009 in San Giuseppe di Comacchio, Ferrara, Italy. The new *Malus* variety was selected by the inventors based on the distinctive fruit characteristic of 'CIVPEAK'. In particular the mature fruits are characterized by an intense purple-red overcolor, extended over a large part of the surface in a flushed and mottled pattern.

Asexual reproduction of the new *Malus* variety by grafting, was first performed in August 2011 in San Giuseppe di Comacchio, Ferrara, Italy, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'CIVPEAK' which in combination distinguish this Apple tree as a new and distinct variety:

1. Intense purple-red colored fruit with flushed and mottled overcolor pattern;
2. More extension of overcolor;
3. Very high eating quality and;
4. Excellent storability and shelf life.

In comparison to the parental variety *Malus* 'CIVNI' (Patented; U.S. Plant Pat. No. 14,177), *Malus* 'CIVPEAK' differs primarily in the traits listed in Table 1.

TABLE 1

| Characteristic | New Variety 'CIVPEAK' | Parental e comparison Variety 'CIVNI' (U.S. Plant Pat. No. 14,177) |
|---|---|---|
| Relative area of overcolor | Very large 80/90% | Medium 60% |
| Pattern of overcolor | Flushed and mottled | Solid flush with strongly defined stripes |
| Hue of overcolor | Purple red RHS 46A | Orange red RHS 33A to RHS 34A |

Of the many commercial varieties known to the present inventor(s), the most similar in comparison to the new *Malus* variety 'CIVPEAK' is the *Malus* variety 'CIVNI', in the following characteristics described in Table 1 above.

BRIEF DESCRIPTION OF THE PHOTOGRAPHS

The accompanying photographs illustrate the overall appearance of the new *Malus* variety 'CIVPEAK' showing the colors as true as is reasonably possible with colored reproductions of this type. Colors in the photographs may differ slightly from the color values cited in the detailed botanical description, which accurately describe the color of 'CIVPEAK'. Trees of 'CIVPEAK' as shown in the photographs are approximately 6 years old.

Figure 1:
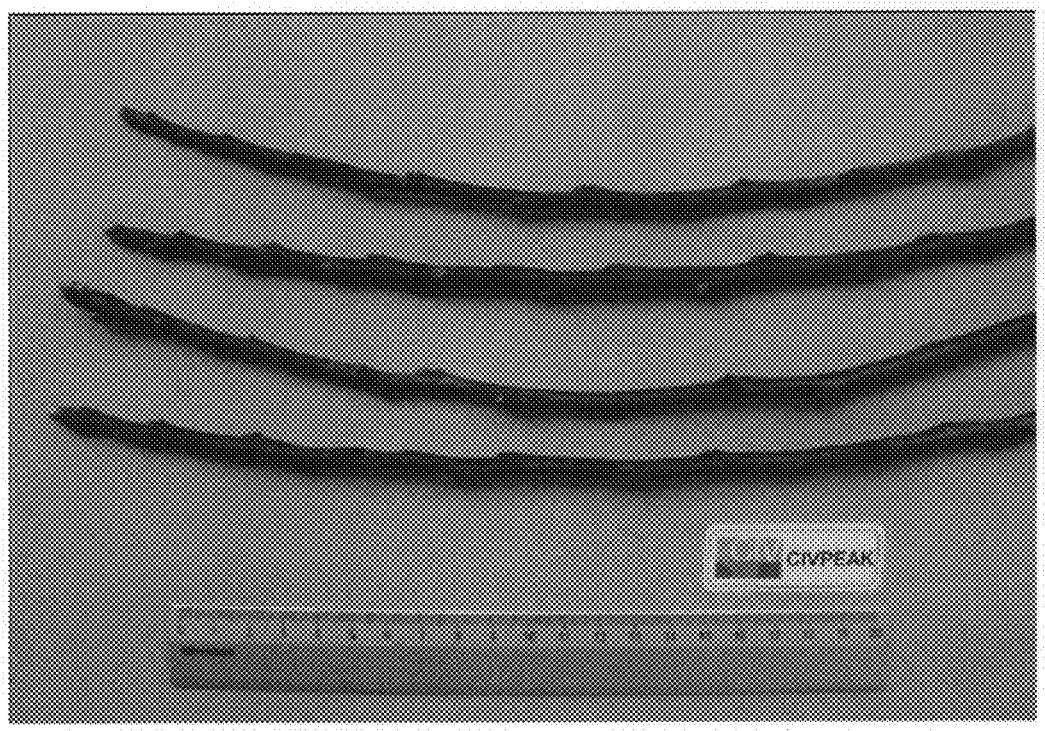
Figure 2:
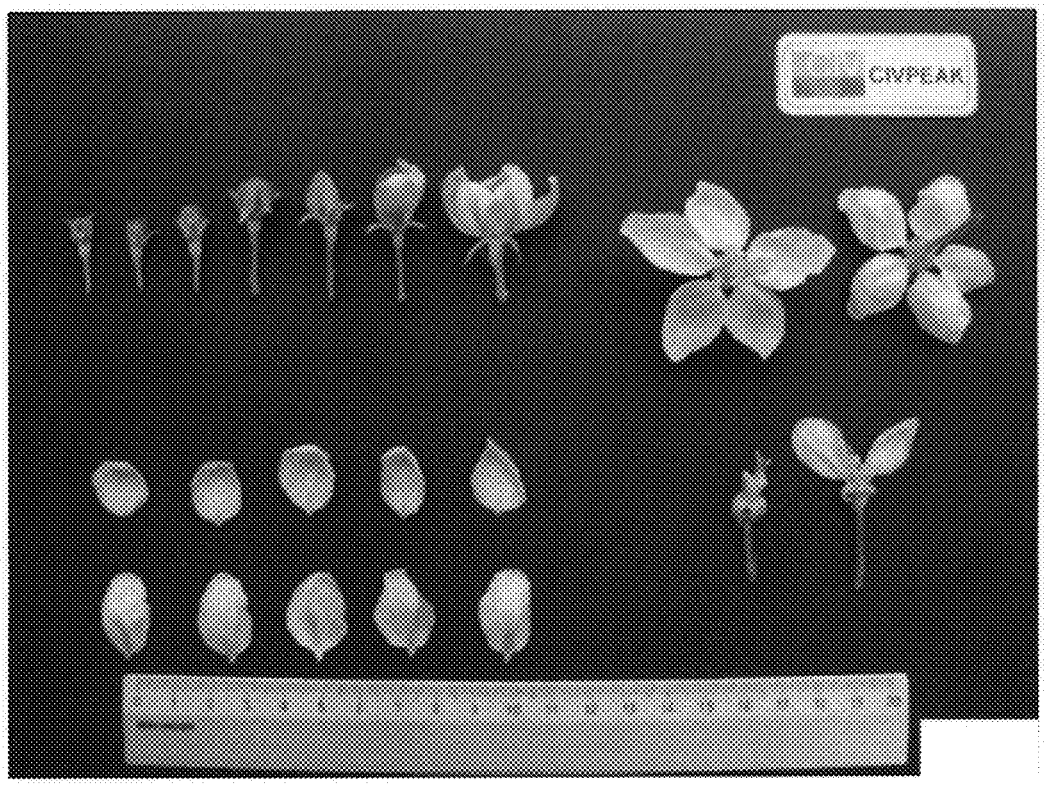
Figure 3:
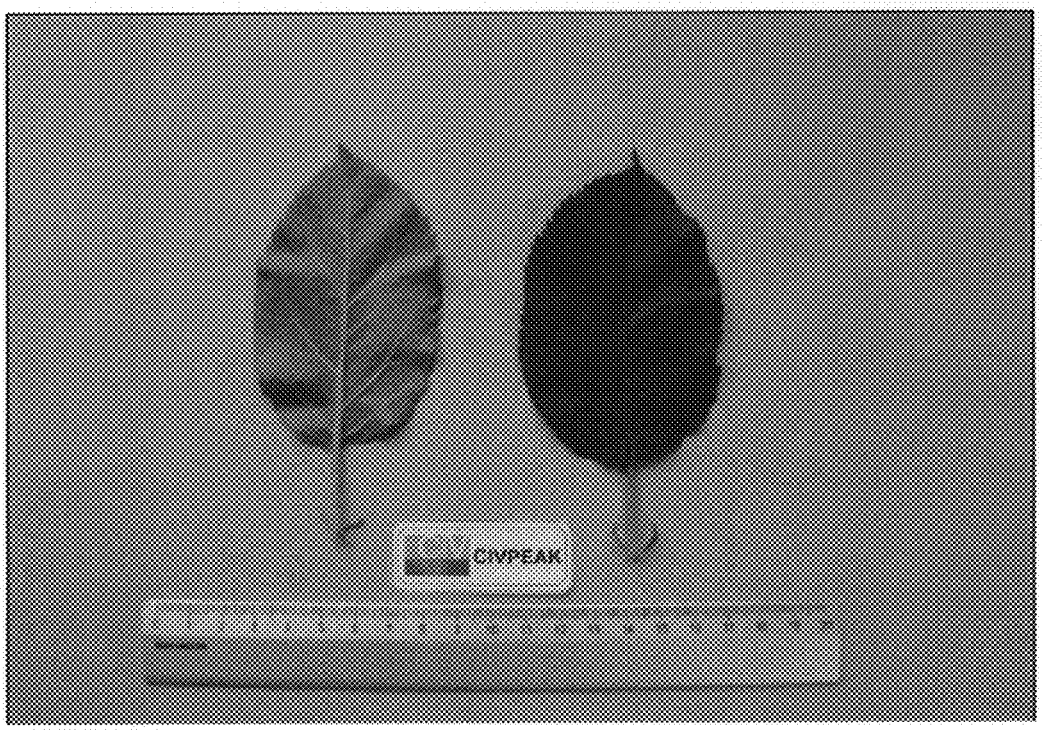
Figure 4:
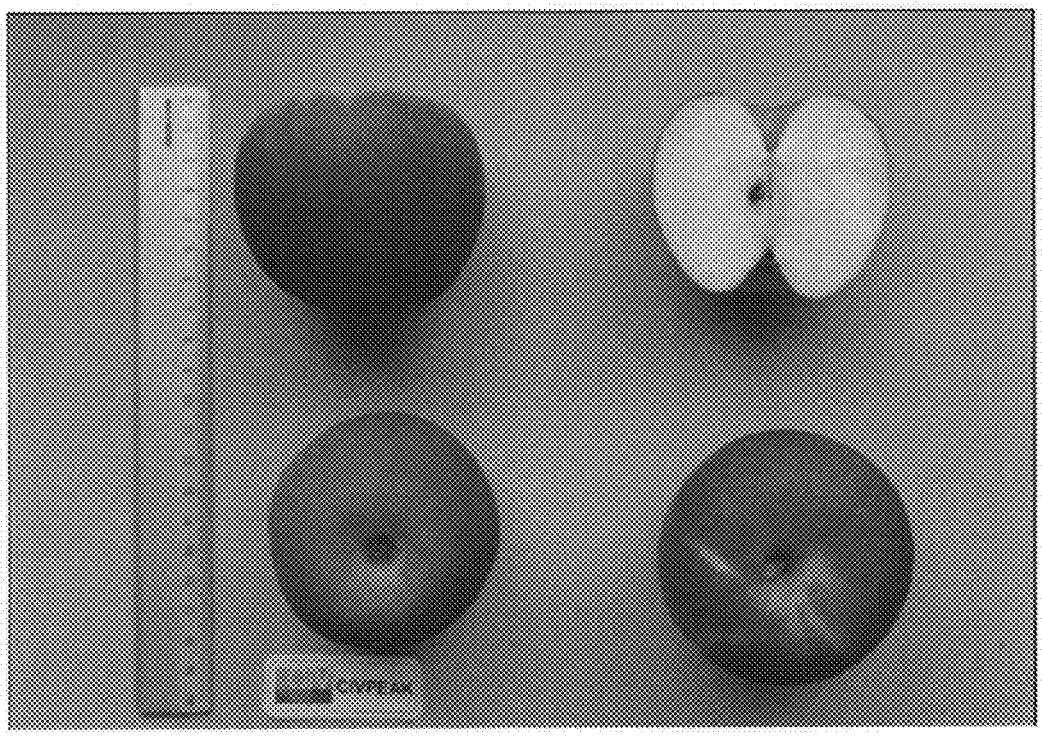

FIG. 1—illustrates typical dormant wood of 'CIVPEAK';
FIG. 2—illustrates typical flowers of 'CIVPEAK'
FIG. 3—illustrates typical leaves of 'CIVPEAK'.
FIG. 4—illustrates typical fruit of 'CIVPEAK'.

DETAILED BOTANICAL DESCRIPTION

The new *Malus* variety 'CIVPEAK' has not been observed under all possible environmental conditions. The phenotype of the new variety may vary with variations in environment such as temperature, light intensity, and day length without any change in the genotype of the Apple tree.

The aforementioned photographs, together with the following observations, measurements and values describe trees of 'CIVPEAK' as grown in the Apple farm in San Giuseppe di Comacchio, Ferrara, Italy, under conditions which closely approximate those generally used in commercial practice. The apple farm where 'CIVPEAK' grow, is situated near the Adriatic sea (44° 45' North, 12° 11' East) and is zero (0) meters above sea level. The soil of the apple farm where 'CIVPEAK' is grown is sandy, and the soil is treated with manure every year and irrigated with drip irrigation systems. The climate is temperate continental with high summer temperatures and low winter temperatures.

Unless otherwise stated, the detailed botanical description includes observations, measurements and values based on 6 year old 'CIVPEAK' trees grown in the Apple farm in San Giuseppe di Comacchio, Ferrara, Italy from 2011 to 2017. Quantified measurements are expressed as an average of measurements taken from a number of trees of 'CIVPEAK'. The measurements of any individual tree, or any group of trees, of the new variety may vary from the stated average.

Color references are made to The Royal Horticultural Society Colour Chart (R.H.S.), 2001 edition except where general colors of ordinary significance are used. Color values were taken under daylight conditions at approximately 10:00 AM in San Giuseppe di Comacchio, Ferrara, Italy.

All of the trees of 'CIVPEAK', insofar as they have been observed, have been identical in all the characteristics described below.

Classification:
Botanical: *Malus domestica* Borkh.
Parentage: Mutation of *Malus* variety designated 'CIVNI'.
Propagation: Grafting.
Growing conditions:
*Light intensities*.—Full sunlight or slight shade.
*Temperature*.—During day, grown in range of 0° C. to 35° C., and during evening, grow in range of −5° C. to 25° C.
*Fertilization*.—The soil in which the trees are grown is sandy, treated with manure every year. With fertigation we make macroelements (N 100 units/ha, P 50 units/ha, K 200 units/ha) and microelements.
*Growth regulators*.—Not use.
*Pruning or trimming requirements*.—Yes.

Tree:
*Age*.—Observed trees were 7 years old.
*Vigor*.—Medium vigor.
*Form*.—Spreading and ramified.
*Habit*.—A medium sized tree with one trunk and 1 leader; main branches spreading.
*Branching habit*.—Main branches angle is 35° to 45° with respect to trunk if allowed to grow naturally.
*Density*.—Medium density.
*Cropping behavior*.—Early beginning production, high productivity and abundant flowering. No biennial bearing.
*Type of bearing*.—Long shoots and spurs.
*Production* (*on* 6 *year*).—About 17.5 kg/tree (2.800 tree/ha).
*Size at maturity*.—Height: About 3.20 m. Spread: About 1.25 m.
*Trunk*.—Height (up to leaders): About 3.20 m. Diameter: About 70 mm, measured 20 cm above the point of engagement. Texture: Smooth. Bark color: RHS 197B.
*Trunk lenticels*.—Length: About 0.75 mm. Width: About 1.38 mm. Color: RHS 164A. Density: About 7 per $cm^2$, measured on the trunk at 1.60 m from the ground.
*Branches*.—Number per tree: About 30. Length: Varies due to pyramidal shape of tree; at 6 years, maximum of 90 cm to 100 cm on the base; minimum of 20 cm to 30 cm on the top. Diameter (at 3 years): About 12 mm to 15 mm. Surface texture: Smooth. Pubescence: Not present. Color: Mature (at 3 years old): RHS 201A. New Growth color: RHS 200A. Internode length: About 1.8 cm to 2.4 cm. Internode diameter: About 5 mm to 6 mm. Branch lenticels: Length: About 1.3 mm. Width: About 0.78 mm. Color: RHS 165A. Density: About 4.5 per $cm^2$.
*Spur*.—Present: Yes. Distance between each spur: On the 2 years old branches, the distance is about 30 mm. Diameter of each spur: About 3.5 mm to 4.5 mm. Number of fruit per spur: About 2 to 4.

Foliage:
*Arrangement*.—Alternate, simple, petiolate.
*Lamina*.—Size: Length: About 91.4 mm (from 87 to 97 mm fully expanded leaf). Width: About 55 mm (from 51 to 61 mm fully expanded leaf). Length/width ratio: 1.66. Overall Shape: Elliptic. Base shape: Broad. Apex shape: Pointed. Margin: Biserrate. Texture: Upper surface: Smooth. Under surface: Hairy. Attitude in relation to shoot: Outwards. Color (mature leaves): Upper surface: RHS 139A. Under surface: RHS 147B. Color (immature leaves): Upper surface: RHS 144A. Under surface: RHS 147C.
*Venation*.—Type: Pinnate venation from central vein to the leaf edge. Color: RHS 146C.
*Petiole*.—Length: About 26 mm. Diameter: About 1.81 mm. Texture: Smooth. Color: RHS 149A.
*Stipule*.—Arrangement: Opposite. Length (distance of stipules from basal attachment of petiole): About 8 mm to 10 mm. Width: About 1.2 mm to 2 mm. Color: Upper surface: RHS 139B. Under surface: RHS 139C.

Inflorescence:

*Blooming time*.—Full bloom on about Apr. 18, 2018.

*Blooming period*.—About 8 to 10 days.

*Fragrance*.—Slight.

*Type*.—Corymb.

*Flower size*.—Large, about 55 mm.

*Flower depth* (*height of the corolla*).—About 22 mm.

*Number of flowers per inflorescence*.—About 5.

*Buds*.—Terminal Buds: Number per spur: About 1. Shape: Rounded. Length: About 5.21 mm. Width: About 4.64 mm. Texture: Hairy. Color: Apex, RHS 199D, and base, RHS 200C.

*Lateral buds*.—Number per spur: About 26. Shape: Pointed but rounded at the end of spur. Length: About 3.74 mm. Width: About 3.82 mm. Texture: Hairy. Color: RHS 166A.

*Petals*.—Arrangement: Free to touching. Number per flower: Five. Size: Length: About 21.9 mm. Width: About 15.4 mm. Length/width ratio: 1.42. Overall shape: Rounded. Apex shape: Rounded. Base shape: Rounded. Texture (upper surface): Smooth. Texture (lower surface): smooth. Margin: Entire. Color (upper surface): Apex, RHS 155D with trace of purple RHS 75B. Color (lower surface): Apex, RHS 155D with trace of purple RHS 75A.

*Sepals*.—Number per flower: Five. Size: Length: About 7.5 mm. Width: About 2.5 mm. Length/width ratio: 3. Overall shape: Recurved downward, pointed acute. Apex shape: Acute. Base shape: Broad. Texture (upper surface): Hairy. Texture (lower surface): Hairy. Margin: Entire. Color (upper surface): RHS 139C with red apex RHS 46A. Color (lower surface): RHS 139C with red apex RHS 46A.

*Pedicel*.—Length: 35 to 28 mm. Diameter: 1.20 to 2.14 mm. Texture: Tomentose. Color: RHS 150D.

Fruit:

*Keeping quality*.—The fruit keeps very well on the tree. It can be stored in cold temperature conditions for up to 7 months without loosing firmness and juiciness. It has a shelf life up to 2 weeks without loosing firmness and juiciness.

*Maturity when described*.—Ripe for eating.

*Maturity period after full bloom*.—About 126 days after full bloom.

*Date of first and last picking* (*harvest*).—From August $8^{th}$ to $14^{th}$ in S.Giuseppe di Comacchio (Ferrara) Italy (North 44° 45'46.2", East 012° 11'31.9") in year 2005).

*Type*.—Pome.

*General shape*.—Conic.

*Average weight*.—About 174.9 g.

*Fruit size*.—Average height: About 65.03 mm. Average diameter (at widest point): About 75.80 mm. Position of maximum diameter: About in the middle height. Height/thickness ratio: 0.85.

*Stem*.—Length: About 16.25 mm. Diameter: About 3.16 mm. Color: RHS 165B.

*Stalk cavity*.—Depth: About 10.57 mm. Width: About 29.4 mm.

*Eye basin*.—Depth: About 7.99 mm. Width: About 34.7 mm. Crowning at calyx end: Weak. Position of sepals: Closed. Calyx tube: Funnel form.

*Skin*.—Thickness: Medium. Texture: Rough. Bloom: Low. Greasiness: Weak. Firmness (at picking time): 7.5 to 8.5 kg/$cm^2$. Overcolor Color: RHS 46A. Percentage of skin surface with overcolor color: About 70 to 90%. Pattern of overcolor: Flushed and mottled. Intensity of overcolor: High. Ground color: RHS 16A. Skin Lenticels: Length: About 0.6 mm. Width: About 0.4 mm. Color: RHS 11A. Density: About 6 per $cm^2$.

*Flesh*.—Color: RHS 11D. Texture: The texture is medium. The type of flesh is firm. Aroma: Aromatic. Eating quality: Good flavor, with a balanced level of acidity and sweetness. Sugar content (at picking time): 14 to 14.5 Brix. Acidity/Starch (at picking time) 7 to 7.5 g/lt. Core: Symmetry of core: Moderately asymmetric. Distinctness of core lines: Medium. Locules: Number (per fruit): 5. Length: About 8.8 mm. Width: About 4.1 mm. Form: Close.

Seeds:

*Number per fruit*.—About 6 to 8.

*Number per locule*.—About 1 to 2.

*Shape*.—Elliptic.

*Length*.—About 9.4 mm.

*Width*.—About 6 mm.

*Texture*.—Smooth.

*Color*.—RHS 166A.

Reproductive organs:

*Androecium*.—Stamen: Number per flower: 16. Length: About 5.75 mm. Color: RHS 157D. Anther: Shape: Ovoid. Length: About 2.17 mm. Color: RHS 13B. Filaments: Length: About 10.4 mm. Color: RHS 149C. Pollen: Amount: Abundant. Color: RHS 10D. Requirements: The apple "Golden Gem" is good pollinator.

*Gynoecium*.—Pistils: Quantity: 5. Length: About 10.8 mm. Color: RHS 149C. Stigmas: Shape: Funnel shape with receptive surface on top. Length: About 1.1 mm. Width: About 0.6 mm. Color: RHS 149B. Ovary: Length: About 1.5 mm. Width: About 1.5 mm. Color: RHS 144A.

Use: Fresh market.

Disease/pest resistance: For both tree and fruit of 'CIVPEAK', no unusual disease/pest resistance observed as of this time.

Disease/pest susceptibility: For both tree and fruit of 'CIVPEAK', no unusual disease/pest susceptibility observed as of this time. Susceptible to scab and slightly susceptible to powdery mildew.

Winter hardiness: Tolerant to temperatures down to −10° C. without observed damage to wood and buds of dormant Apple trees, depending on the length of exposure.

Drought/heat tolerance: Tolerant to temperatures up to 35° C., growth is limited by drought periods without irrigation.

Shipping/storage characteristics: Good storability under ULO-conditions (1° C., 2% $O_2$, 2% $CO_2$) for seven (7) months.

We claim:

1. A new and distinct variety of *Malus domestica* Borkh apple tree named 'CIVPEAK', as illustrated and described herein.

* * * * *